United States Patent [19]

Makuuchi et al.

[11] 4,129,487

[45] Dec. 12, 1978

[54] PROCESS FOR IMPROVING THE PROPERTIES OF AN AQUEOUS EMULSION TYPE COATING COMPOSITION

[75] Inventors: Keizo Makuuchi, Sakai; Kunio Araki, Takasaki; Tohru Takagi; Hiroyuki Nakayama, both of Hiratsuka; Haruo Kozu, Fujisawa, all of Japan

[73] Assignee: Japan Atomic Energy Research Institute, Tokyo, Japan

[21] Appl. No.: 661,153

[22] Filed: Feb. 25, 1976

[30] Foreign Application Priority Data

Feb. 28, 1975 [JP] Japan .................................. 50-24528

[51] Int. Cl.$^2$ .............................................. C08F 8/00
[52] U.S. Cl. ........................... 204/159.14; 204/159.20; 427/44; 427/372 R; 427/388 A; 427/388 C; 428/442
[58] Field of Search ...................... 204/159.22, 159.14, 204/159.20; 427/44, 372 R, 388 A, 388 C

[56] References Cited

U.S. PATENT DOCUMENTS

| 3,042,652 | 7/1962 | Pariser et al. ................. 204/159.2 X |
| 3,165,487 | 1/1975 | Gardner et al. .............. 204/159.2 X |
| 3,297,613 | 1/1967 | Gibbs ................................... 260/29.6 |
| 3,311,579 | 3/1967 | Donat ......................... 204/159.22 X |
| 3,503,918 | 3/1970 | Le Sota et al. ...................... 260/29.7 |
| 3,725,229 | 4/1973 | Kehr et al. ....................... 204/159.14 |
| 3,819,498 | 6/1974 | Domine et al. ................. 204/159.14 |

*Primary Examiner*—Murray Tillman
*Assistant Examiner*—Thurman K. Page
*Attorney, Agent, or Firm*—Stevens, Davis, Miller & Mosher

[57] ABSTRACT

A process for producing an aqueous emulsion type coating composition, which can form a film having excellent resistance to chemicals and water, which comprises irradiating the aqueous emulsion containing at least one radiation-crosslinkable resin and not containing substantial amounts of a stabilizer having a hydroxy group, such as cellulose and polyvinyl alcohol, by means of ionizing radiation.

3 Claims, No Drawings

PROCESS FOR IMPROVING THE PROPERTIES OF AN AQUEOUS EMULSION TYPE COATING COMPOSITION

BACKGROUND OF THE INVENTION

This invention relates to a process for producing an improved aqueous emulsion coating composition which can form film having excellent resistance to chemicals and water.

The use of an organic solvent type coating composition may be restricted hereafter in order to prevent environmental pollution. Therefore, the development of an aqueous coating composition not containing an organic solvent has been demanded.

In the prior art, an aqueous emulsion type coating composition not containing an organic solvent has been prepared. The use of the aqueous coating composition is preferred in respect to preventing the environmental pollution, because no organic solvent is used in a process for preparing the aqueous coating composition. Also, no special facilities such as, solvent-removing means are necessary when using the aqueous coating composition. A variety of aqueous emulsion type coating compositions are used in practice for the foregoing reasons.

However, aqueous emulsion type coating compositions are inferior to the organic solvent type coating composition in resistance to chemicals and particularly resistance to water. A non-soap type emulsion coating composition and a low soap concentration emulsion coating composition have been developed for overcoming the above disadvantages. However, the compositions of this type still have the above mentioned disadvantages, so they are neither usable outdoors nor as a top coating.

A process which comprises coating a composition containing a radiation-sensitive prepolymer, such as an unsaturated polyester on a substrate, and then irradiating the resulting coating by means of ionizing radiation has also been developed. In practicing such process, an electron-generating apparatus, a radiation-shielding apparatus and an apparatus for securing an inert atmosphere are necessary on the spot at which said composition is coated. However, setting these apparatuses on the spot is expensive, so irradiation of the coating by means of ionizing radiation in situ was impossible in practical use. In addition, since electron beam has low permeability, and tends to go straight, it was difficult to irradiate the resin coated on a curved surface or at a joint with an electron beam.

In the prior art, an aqueous emulsion type coating composition usually contained a stabilizer having hydroxy groups, such as hydroxyethyl cellulose or polyvinyl alcohol.

When the aqueous emulsion type coating composition containing said stabilizer was irradiated with an ionizing radiation, the viscosity of the emulsion increased. In some cases, the emulsion composition changed to a semisolid state, such as a gelatinous state or a pudding-like state. Neither such emulsion composition having high viscosity nor such emulsion composition in a semisolid state was usable as a coating composition.

In general, when an emulsion composition containing a crosslinkable resin was irradiated with an ionizing radiation, the crosslinkable resin molecules contained in each dispersed particle in the emulsion composition crosslinked to one another. That is, each particle in the emulsion composition gave rise to gelation, and became rigid. Therefore, the film-forming properties of the emulsion composition were lost. For the reasons mentioned above, the prior art was defective in that when the aqueous emulsion type coating composition was irradiated with ionizing radiation, the film-forming properties of the composition were lost.

SUMMARY OF THE INVENTION

The inventors of the present invention have carried out a variety of research and experiments. As a result, the inventors have found that when the aqueous emulsion type coating composition not containing substantial amounts of a stabilizer having hydroxy group, such as polyvinyl alcohol was irradiated with ionizing radiation, the properties of the coating composition were improved. This invention is formed on the basis of this discovery.

The term "properties of an aqueous emulsion type coating composition" in the specification and the claims means the film-forming property of the coating composition and the resistance to chemicals and water of the film formed by coating the coating composition on a substrate.

Therefore, one object of this invention is to provide a process for improving the properties of an aqueous emulsion type coating composition.

Another object of this invention is to provide a process for producing an aqueous emulsion type coating composition which can form a film having excellent resistance to chemicals and water.

This invention relates to a process for improving the properties of an aqueous emulsion type coating composition containing at least one radiation-crosslinkable resin, characterized in that the coating composition does not contain substantial amounts of a stabilizer having hydroxy group and the composition is irradiated with ionizing radiation before coating the composition on a substrate.

A DETAILED DESCRIPTION OF THE INVENTION

According to the present invention, though the crosslinkable resin molecules contained in each dispersed particle in the emulsion composition crosslink to one another, the film-forming property of the composition is not lost because the viscosity of the composition increases very little. That is, the film-forming property of emulsion composition irradiated with ionizing radiation according to the present invention is the same as that of the non-irradiated coating composition. The clarity of the film formed by coating the irradiated coating composition on a substrate is substantially the same as that of the film formed by coating the non-irradiated coating composition on a substrate. In addition, the irradiated film is superior to the non-irradiated film in resistance to chemicals and water and resistance to top-coat. The term "film has resistance to top coat" means that when other coats are formed on the film, the film is resistant to the other coats.

The emulsion type coating composition of this invention means what is called an emulsion coating composition. The emulsion type coating composition of this invention includes one obtained by emulsion-polymerizing one or more monomers and the one obtained by emulsifying the polymer prepared by another polymerizing process. That is, the good emulsion coating composition may be formed by applying the process of this invention to the emulsion prepared by any method. The process for producing emulsion employed in the present invention is decided by a process for polymerizing the monomer employed, the physical properties of the resin and economic point of view.

The emulsion composition prepared by emulsion-polymerization of a monomer contains a small amount of the unreacted monomer. When such composition containing the unreacted monomer is coated on a substrate without irradiating the composition with ionizing radiation, bad odor caused by the evaporation of the monomer is generated. However, when the irradiated coating composition is coated on a substrate, such bad odor is not generated because the unreacted monomer remaining in the composition polymerizes during irradiation.

It is critical in the present invention that a resin constituting the coating composition be a radiation-crosslinkable resin. The radiation-crosslinkable resin may be a thermoplastic resin or a thermosetting resin, or a mixture thereof.

Representative radiation-crosslinkable resins include homopolymers of a monomer, such as an acrylate, methacrylate, vinyl acetate, VeoVa, vinyl chloride, or ethylene, and copolymers of these monomers. When even a monomer forming a radiation-decomposable resin by polymerization, for example a methacrylate such as methyl methacrylate copolymerizes with a monomer capable of forming a radiation-crosslinkable resin, a radiation-crosslinkable copolymer or resin may be formed.

The proportion of the resin in the emulsion is not critical. However, advantageously the proportion of the resin in the emulsion may range from 30% to 60% by weight on the basis of weight of the composition, considering the properties of the coating composition.

The coating composition used in this invention may contain an anionic, cationic or non-ionic emulsifying agent in place of the stabilizer having hydroxy groups in order to maintain the composition in an emulsion state. The kinds of the emulsifying agent and amount of the agent added to the composition are not critical. The well known emulsifying agents are usable in this invention. Considering the film-forming property of the coating composition, the proportion of the emulsifying agent added may be less than 10% by weight, preferably less than 5% by weight on the basis of weight of the composition. When a particular resin is used, a stable emulsion may be obtained without using the emulsifying agent.

In the present invention, it is necessary that the coating composition not contain substantial amounts of a stabilizer having a hydroxy group, such as polyvinyl alcohol or a cellulose derivative. The description "the composition does not contain substantial amount of the stabilizer" means that the composition contains less than 0.5% by weight of the stabilizer on the basis of the weight of the composition. The reason is that when a composition containing more than 0.5% by weight of the stabilizer is irradiated with ionizing radiation, the viscosity of the composition increases considerably, that is, the composition changes to a semi-solid state. When the composition containing less than 0.5% by weight of the stabilizer is irradiated with ionizing radiation, the viscosity of the composition increases very little.

A pigment, such as titanium white or mica; a polymerization initiator; and a plasticizer, such as dioctyl phthalate may be added to the composition before or after irradiation. Well-known pigments, plasticizer and polymerization initiators are usable in this invention. The ionizing radiation used in the present invention may include electron beam, alpha rays, beta rays, gamma rays or X rays. Electron beam and gamma rays are preferred. The total dose of the radiation depends on the components of the emulsion employed, the radiation atmosphere, the radiation temperature, degree of crosslinking the resin and the cost of radiation facilities. The total dose of the radiation may range from $10^4$ to $10^8$ rad, but a total dose in the range of from $10^5$ to $10^7$ rad is preferred.

The irradiation may be effected within the temperature range over which the emulsion is stable. The irradiation may be effected in an inert atmosphere. Also the irradiation may be effected at room temperature in air. It may be necessary that the composition of this invention is maintained in a stable emulsion state during or after irradiation. The temperature range over which the emulsion is stable was known to those skilled in the art. When the emulsion composition irradiated according to this invention is heated, the degree of crosslinking further increases. However, a desirable degree of crosslinking can be obtained without heating the irradiated composition.

The emulsion coating composition produced according to this invention may be coated on a substrate by means of brushing, spraying or dipping in the same way as with the prior art emulsion coating composition.

Though the crosslinking of the resin molecules in the film formed by coating can be promoted by drying the film at an elevated temperature, the desired object can be achieved by drying the film at room temperature.

This invention is further illustrated by the following Examples. However, this invention should not be limited by these examples, and changes and modifications within the spirit and scope of the claim can be effected. The percents and parts in the Examples are based on weight unless otherwise specified.

EXAMPLE 1

Into a reactor were charged 233 parts of water, 100 parts of ethyl acrylate, 3 parts of polyethylene phenyl ether nonionic surfactant (EA- 190 D, Daiichi Industry Chemicals Co.) as an emulsifying agent and 0.5 parts of acid sodium sulfite as a polymerization initiator. The monomer was polymerized by radical polymerization to form polyethyl acrylate emulsion. The concentration of the polymer was 30.3%.

In accordance with the test of Japanese Industrial Standards K 5400, the emulsion was distributed among bubble viscometers as specified in the Standards. Some of the viscometers were irradiated with gamma rays from a Co 60 source at a total dose as shown in Table 1. The irradiated viscometers were rotated on their axes by an angle of 180°. The rate ($V_1$) of the bubble rising in the rotated viscometer was measured. Similarly the rate ($V_0$) of the bubble rising in the non-irradiated viscometer was measured. The ratio of $V_1$ to $V_0$ was calculated.

Portions of said emulsion were irradiated with gamma rays from a Co 60 source for a total dose as shown in Table 1. The film-forming property and the brushing property of each one of the irradiated emulsion compositions were determined by brushing the composition on a glass plate, followed by drying the coating at a temperature of 100° C. in air.

The gel percent of each one of the irradiated compositions was determined as in the following.

Each of the irradiated emulsions was dried, and the resulting dried mass (Wo gr) was wrapped in metal wire made of stainless steel. Each mass was boiled in boiling acetone for 24 hours to extract the soluble portion in the mass.

The resulting mass was dried in vacuo, and was weighed ($W_1$). The gel percent was calculated by the ratio of $W_1$ to $W_0$. The non-irradiated emulsion composition was treated in the same way as that as above mentioned.

As control tests, the non-irradiated emulsion was coated on a glass plate and was dried. The resulting film was divided into several pieces. Each of the pieces was irradiated with gamma rays for a total dose as shown in Table 1 in vacuo. Gel percent of each of the pieces was determined as mentioned above. The results are shown in Table 1.

Table 1

| Total dose (Mrad) | Ratio of $V_1$ to $V_0$ | Brushing property | Film-forming property | Gel percent emulsion | film* |
|---|---|---|---|---|---|
| 0 | 1.0 | excellent | excellent | 0 | 0 |
| 1 | 1.0 | " | " | 44 | 20 |
| 2 | 1.0 | " | " | 50 | 37 |
| 3 | 1.0 | " | " | 55 | 45 |
| 4 | 1.0 | " | " | 58 | 48 |
| 6 | 1.0 | " | " | 63 | 59 |
| 16 | 1.0 | " | " | 78 | 77 |

Note: *Control test

The increase in viscosity of the emulsion irradiated with gamma rays for a total dose of 16 Mrad was hardly detectable. The film-forming properties and the brushing properties of said emulsion were excellent.

The gel percent of the irradiated emulsion was higher than that of the film obtained by coating the non-irradiated emulsion on a glass plate, then irradiating the coating. This shows that the film obtained by coating the irradiated emulsion on a glass plate has excellent resistances to chemicals and water. This is important.

EXAMPLE 2

The procedure of Example 1 was repeated except that a commercially available aqueous emulsion (It is sold under trade name of AC-248 from Daiseru Co.) containing 47% of copolymer of methyl methacrylate (30%) and ethyl acrylate (70%) and non-ionic emulsifier was employed. The results are shown in Table 2.

Table 2

| Total dose (Mrad) | Ratio of $V_1$ to $V_0$ | Brushing property | Film-forming property | Gel percent emulsion | film* |
|---|---|---|---|---|---|
| 0 | 1.0 | excellent | excellent | 0 | 0 |
| 0.75 | 1.0 | " | " | 77 | 0 |
| 1.5 | 1.0 | " | " | 80 | 35 |
| 3.0 | 1.0 | " | " | 85 | 35 |

Note: *Control test

Poly(methyl methacrylate) is a radiation-decomposable resin. However, the copolymer of methyl methacrylate and ethyl acetate is a radiation-crosslinkable resin. When the copolymer was irradiated with gamma rays, a resin having high gel percent was obtained.

EXAMPLE 3

To the emulsion employed in Example 2 was added White Pigment (produced by Kansai Paint Co.) comprising titanium white, mica, clay and calcium carbonate in the amount equal to that of the resin in the emulsion. The resulting mixture was sufficiently stirred to form a white coating composition, and 8 cc of the coating composition was charged into aluminum cans. These aluminum cans were irradiated with gamma rays for a total dose as shown in Table 3. The physical properties of the film obtained by coating the irradiated coating composition on a glass plate were determined. The results are shown in Table 3.

Table 3

| Total dose (Mrad) | Film-forming property | Adhering force(1) (%) | Resistance to water(2) | Resistance to alkali(3) | Resistance to top coat (4) |
|---|---|---|---|---|---|
| 0 | excellent | 100 | poor | poor | fairly good |
| 1 | excellent | 90 | good | good | good |
| 6 | excellent | 80 | good | good | good |
| 16 | excellent | 80 | good | good | good |

Note:
(1) The emulsion was coated on a metal substrate to form a film.
The resulting film adhering to the metal was slitted at right angles to make a checkerboard pattern at an interval of 1 mm. Adhesive cellophene tape was temporarily adhered on the slitted film, and was removed therefrom. The percent of the remaining film on the metal is expressed as "Adhereing force".
(2) The coated substrate was soaked in tap water at a temperature of 10° C. Thereafter, the substrate was scrubbed with fingers.
Estimate:
  poor — The film was changed to white.
  good — The film was not changed.
(3) The coated substrate soaked in a solution of saturated cupric hydroxide for one week.
Estimate:
  poor — The film was blistered.
  good — The film was not changed.
(4) The test was effected on the basis of Japanese Industrial Standards K 5400.
Estimate:
  good — When coating emulsion was coated on the same substrate two times, cracking, blistering and peeling of the film were not detected.
  fairly good — Cracking, blistering and peeling of the film were slightly detected.

It is apparent from Example 3 that when the emulsion was irradiated with gamma rays, the resistance to alkali and water, and resistance to top coat of the film were improved.

EXAMPLE 4

1% of each of sodium dodecylsulfate (anionic emulsifier), cetyl trimethylammonium chloride (cationic emulsifier) and polyethylene glycol lauryl ether (non-ionic emulsifier) were added to vinyl acetate. The vinyl acetate was emulsion-polymerized using ionizing radiation. Each of the resulting polyvinyl acetate emulsions were irradiated with gamma rays for a total dose of 6 Mrad. Gel percent of each of the irradiated emulsions were determined. The results are shown in Table 4.

Table 4

| Emulsifier | Gel percent |
|---|---|
| sodium dodecylsulfate (anion) | 53 |
| cetyl trimethylammonium chloride (cation) | 48 |

Table 4-continued

| Emulsifier | Gel percent |
|---|---|
| polyethylene glycol lauryl ether (non-ion) | 50 |

Since the gel percents of the three emulsions before crosslinking are different from one another, the gel percents of the three emulsion after crosslinking are different from one another. However, it is apparent from Table 4 that the emulsion is subjected to gelation by irradiating it with gamma rays.

COMPARATIVE EXAMPLE 1

This Example shows that it is essential that the emulsion coating composition be used without breaking the emulsion state.

To one part of the irradiated emulsion employed in Example 2 was added 10 parts of acetone, thereby obtaining a clear liquid. This shows that the emulsion state was broken. When the clear liquid was coated on a glass plate, cracking in the resulting film was detected.

On the other hand, when the same procedure was repeated using the non-irradiated emulsion, a uniform film was formed.

COMPARATIVE EXAMPLE 2

To the polyethyl acrylate employed in Example 1 was added polyvinyl alcohol having polymerization degree of 500 in various amounts. The relationship between the concentrations of polyvinyl alcohol and the properties of film obtained by coating the emulsion on a substrate was examined. When the concentration of polyvinyl alcohol was more than 1%, the viscosity of the emulsion increased as the irradiation continued. When the total dose of the radiation reached 3 M rad, the emulsion became pudding-like. The pudding-like emulsion could not be brushed. The gel percent of the emulsion containing 0.5% of polyvinyl alcohol was lower than that of the emulsion not containing polyvinyl alcohol by 10%. When the concentration of polyvinyl alcohol was more than 0.5%, the gel percent of the emulsion was strikingly lowered. When the concentration of polyvinyl alcohol was less than 0.5%, the viscosity of the emulsion increased very little and the gel percent of the emulsion is somewhat lowered.

When hydroxyethyl cellulose was added to the emulsion, the viscosity of the emulsion decreased as irradiation of the emulsion continued, and therefore, the rate of gelation of the emulsion became slow. The tendency became striking, when the concentration of hydroxyethyl cellulose was more than 0.5%.

Therefore, it is apparent from Comparative Example 2 that addition of polyvinyl alcohol or hydroxyethyl cellulose to the emulsion impairs the properties of the film obtained by coating the emulsion on a substrate and the handling property of the emulsion. However, addition of less than 0.5% of polyvinyl alcohol or hydroxyethyl cellulose can be allowed.

What we claim is:

1. A process for improving the properties of an aqueous emulsion type coating composition containing from 30% to 60% by weight of at least one radiation crosslinkable resin, selected from the group consisting of homo- or co-polymers of an acrylate, vinyl acetate, versatic acid, vinyl chloride and ethylene, wherein said coating composition contains less than 0.5% by weight of a stabilizer having hydroxy groups on the basis of weight of the composition and the composition is irradiated with ionizing radiation at a total dose in the range of from $10^4$ rad to $10^8$ rad before coating the composition on a substrate, said composition being and maintained in a stable emulsion state during and after irradiation.

2. The process defined in claim 1 wherein the resin is a radiation-crosslinkable copolymer of a methacrylate and at least one monomer capable of forming a radiation-crosslinkable resin.

3. The process defined in claim 1 wherein the ionizing radiation is electron beam or gamma rays.

* * * * *